United States Patent
Larsson

Patent Number: 5,830,206
Date of Patent: *Nov. 3, 1998

[54] PANTS-TYPE DIAPER OR SANITARY PANTY

[75] Inventor: Björn Larsson, Billdal, Sweden

[73] Assignee: Mölnlycke AB, Göteborg, Sweden

[*] Notice: This patent issued on a continued prosecution application filed under 37 CFR 1.53(d), and is subject to the twenty year patent term provisions of 35 U.S.C. 154(a)(2).

[21] Appl. No.: 714,183
[22] PCT Filed: Apr. 11, 1995
[86] PCT No.: PCT/SE95/00392
§ 371 Date: Oct. 4, 1996
§ 102(e) Date: Oct. 4, 1996
[87] PCT Pub. No.: WO95/27463
PCT Pub. Date: Oct. 19, 1995

[30] Foreign Application Priority Data

Apr. 12, 1994 [SE] Sweden .................................. 9401228

[51] Int. Cl.$^6$ ........................................................ A61F 13/15
[52] U.S. Cl. ............................ 604/390; 604/389; 604/311
[58] Field of Search ........................ 604/385.1, 389–391, 604/393–396; 24/305, 306, 704.1, 704.2

[56] References Cited

U.S. PATENT DOCUMENTS

| 3,931,666 | 1/1976 | Karami | 604/389 |
| 3,989,048 | 11/1976 | Cepuritis et al. | 604/390 |
| 3,999,546 | 12/1976 | Feldman et al. | 604/396 |
| 4,020,842 | 5/1977 | Richman et al. | 604/396 |
| 4,049,001 | 9/1977 | Tritsch | 604/390 |
| 4,699,622 | 10/1987 | Toussant et al. | 604/389 |
| 4,801,480 | 1/1989 | Panza et al. | 604/390 |
| 5,358,500 | 10/1994 | Lavon et al. | 604/385.1 |
| 5,370,634 | 12/1994 | Ando et al. | 604/396 |
| 5,620,432 | 4/1997 | Goulait et al. | 604/389 |

FOREIGN PATENT DOCUMENTS

| 1 379 689 | 1/1975 | United Kingdom . | |
| 2267024 | 11/1993 | United Kingdom | 604/396 |

Primary Examiner—John G. Weiss
Assistant Examiner—K. M. Reichle
Attorney, Agent, or Firm—Burns, Doane, Swecker & Mathis, L.L.P.

[57] ABSTRACT

The present invention relates to an absorbent article in the form of a pants-type diaper or sanitary panty, which includes an elongated absorbent body (1) enclosed between two casing sheets (2, 3) which include side parts (7–10) which at opposing front and rear end parts of the absorbent body extend laterally beyond the body on both sides thereof. According to the invention, opposing front and rear side parts (7, 9 and 8, 10 respectively) are joined together by a fastener element (11) which is attached to one of the mutually opposing side parts by a first, strong join (12) and releasably and refastenably joined to the other side part by means of a second join (13) which is weaker than the first join.

12 Claims, 2 Drawing Sheets

PANTS-TYPE DIAPER OR SANITARY PANTY

BACKGROUND OF THE INVENTION

The present invention relates to an absorbent article in the form of a pants-type diaper or a sanitary panty which comprises an elongated absorbent body enclosed between two casing sheets which at opposing front and rear end parts of the absorbent body have side parts which extend laterally beyond the absorbent body on both sides thereof.

So-called all-in-one diapers are being replaced to an ever greater extent with pants-type diapers, or so-called trainers, for slightly older diaper-wearing children. Pants-type diapers have a number of good features. They fit well on the wearer, they are easy to put on and take off with the child in a standing position, they sit firmly in place after having been put onto a child, and conform to the anatomy of the child as the child moves, in a comfortable fashion. Moreover, pants-type diapers resemble conventional underpants and it is easy to understand how they shall be used, thereby in many instances enabling somewhat older diaper-wearing children to perform themselves the simple operations required in putting on the diaper. However, pants-type diapers, or trainers, also have certain drawbacks. They are difficult to change while the user is lying on his/her back and, when changing the diaper, require any garment that is worn on top of the diaper to be removed completely. Neither can a used pants-type diaper be rolled-up and sealed in the same manner as an all-in-one diaper. In addition, a dirty pant diaper which contains feces is liable to soil the wearer when removing the diaper.

OBJECTS AND SUMMARY

An object of the present invention is to eliminate the aforesaid drawbacks.

According to the present invention, this object is achieved in that an absorbent article in the form of a pants-type diaper or a sanitary panty, wherein mutually opposing front and rear side parts are joined together through the medium of a fastener element which is joined to one of the mutually opposing side parts by means of a first, strong join or fastening and can be released from and refastened to the other side part by means of a second join or fastening which is weaker than the first join, is characterized in that the second join includes a first fastener means which is destroyed when the second join is opened for the first time, and a second refastenable fastener means which cannot be opened for a first time without destroying the first fastening.

According to a preferred embodiment of the invention, the second join is stronger in a non-released state than when resealed after being released for the first time. The first fastener means is comprised of a weld join or a glue join and the second fastener means is comprised of a mechanical fastener type and the mechanical fastener is the fastening type. The fastener element is preferably comprised of the male part of a ribbon-like self-fastening fastener, i.e. that part of such a fastener which includes a large number of hooks projecting from one surface thereof, and the female part of the self-fastening fastener is comprised of a nonwoven material which forms a casing sheet of the article at the same time.

BRIEF DESCRIPTION OF THE DRAWINGS

The invention will now be described in more detail with reference to the accompanying drawings, in which.

DETAILED DESCRIPTION OF THE PREFERRED EMBODIMENTS

Figure 1:
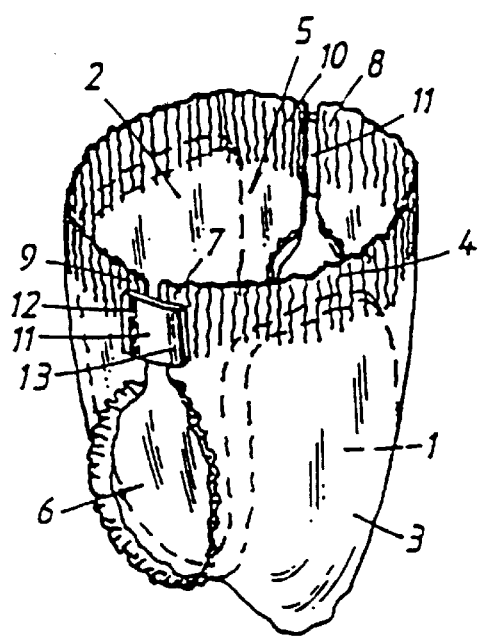
FIG. 1 is a perspective view of one embodiment of an inventive pants-type diaper.

FIG. 1 is a perspective view of a first embodiment of an inventive pants-type diaper. A pants-type diaper is intended to be put on in the same way as a pair of underpants, and is characterized by an elastic waist part which can be stretched so as to enable the pant diaper to be easily drawn over the wearer's hips when putting on and removing the pant diaper, and which is so elastic as to ensure that when worn the pant diaper will be held securely in place by the contraction forces exerted by the elastication in the waist part of the pant diaper. In order to fulfil these functional requirements while, at the same time, limiting the number of product sizes, the pant diaper will preferably have a stretch which is greater than 80%, i.e. it shall be possible to stretch the waist part to an extent which corresponds to 1.8 times the circumference of the waist part of a pants-type diaper in a relaxed state. When the pant diaper is worn, the combined contraction force in the waist part, i.e. the sum of the forces exerted by the elastic provided in the front part, the rear part and the side parts of the pant diaper, will preferably exceed 3N.

The pants-type diaper illustrated in FIG. 1 is constructed in the same way as the pants-type diaper described in Swedish Patent Application No. 9200663-4, and includes an absorbent body 1 enclosed between an inner and an outer casing sheet 2 and 3 respectively. The inner casing sheet 2 is liquid-permeable and is comprised, for instance, of non-woven material compiled from fibres of polyethylene, polypropylene, polyester or mixtures thereof. Viscose fibres may also be used. It is also conceivable to use a perforated plastic sheet, for instance a perforated polyethlylene sheet for the inner casino sheet. The, outer casing sheet 3 is liquid-impermeable or at least hydrophobic and may, for instance, comprise a sheet of polyethylene or nonwoven material which has been coated with or laminated with polyolefins, so as to be made liquid-impermeable or at least hydrophobic. For aesthetic and psychological reasons, the outer casing sheet 3 may be comprised of two layers, an inner liquid-impermeable layer and a layer of fabric-like material disposed outside the inner layer. Thereby, the user will see and feel the pant diaper as less plastic. When the outer casing sheet has this latter construction, it is not necessary for the liquid-impermeable sheet to have the same extension as the fabric-like sheet, but may be smaller than said sheet, for instance liquid-impermeable casing material can be omitted from the side parts of the pant diaper.

The absorbent body 1 may contain cellulose fluff pulp with or without an admixture of particles of so-called superabsorbent material and/or thermoplastic melt fibres. The absorbent body 1 may be comprised of one or more layers.

The waist part 4 of the pants-type diaper illustrated in FIG. 1 includes a plurality of sequentially mounted elastic threads, each of which extends transversely around the circumference of the waist part. A relatively broad elastic waist part is formed in this way. As will be understood, elastic ribbons, bands or the like may be used instead of elastic threads, or other elastically stretchable material can be used, such as elastically stretchable plastic film, an elastically stretchable nonwoven material, or like material.

Similar to a pair of underpants, the pants-type diaper illustrated in FIG. 1 has a waist opening 5 and two leg openings 6 which are provided with leg elastic in a conventional manner. The pant diaper is put on by inserting the legs of the wearer through the leg openings 6 and then drawing the diaper up over the wearer's hips. The contraction forces exerted by the elastic elements at the waist opening, i.e. at the uppermost part of the waist part 4, are preferably greater than the contraction forces acting in the remainder of the waist part. This will ensure that the pant diaper remains seated in its intended position, even when the absorbent body is full of urine.

Figure 6:
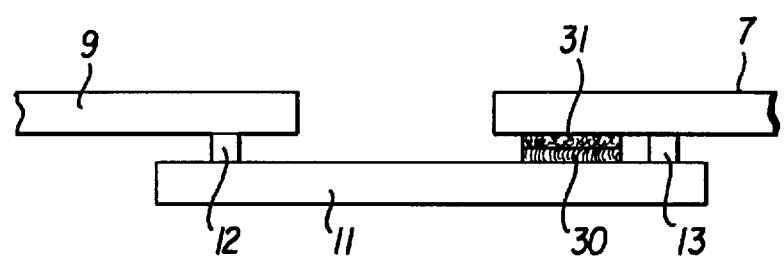
FIG. 6 is a schematic view from above of the portion of FIG. 1 that includes one of the fastener bands.

According to the invention, the front side parts 7, 8 of the pants-type diaper are joined to respective opposing rear side parts 9 and 10 by means of a fastener band 11. In the case of,the illustrated embodiment, the fastener bands 11 comprise VELCRO® fasteners. That side of the bands 11 that faces towards the outer casing sheet 3 includes a large number of sponge-like projections which grip in the meshes of the nonwoven material from which the casing sheet is preferably comprised and forms a releasable and refastenable join or fastening between the fastener bands 11 and respective side parts 7–10 (FIG. 1) or fastener bands 11 and respective side part 7 (FIG. 6) and side part 8. Other types of self-fastening fastener means which include male and female parts that present hooks 30 and eyes 31 respectively may also be used, of course, wherein the female parts are attached to the outer casing sheet.

In addition to being fastened to the side parts by self-fastening fasteners, the bands 11 are also welded or glued to the rear and front side parts as shown at 12 and 13 respectively. The joins 12 which fasten the bands 11 to respective rear side parts 9, 10 are extremely strong and are able to safely resist the loads to which the pant diaper can be subjected in use. Preferably, this join, or fastening, will be so strong that it cannot be broken without tearing the band or the casing material, and can therefore be considered to provide a permanent join in practice. The joins, or fastenings, 13 which join the bands 11 to the respective front side parts 7 and 8 are much weaker than the aforesaid joins and function to ensure that the self-fastening type fasteners located between the forward part of each front side part and corresponding part of the bands 11 are not released unintentionally in normal use of the pant diaper. When the pant diaper is used, these latter joins arm subjected to the heaviest loads as the pant diaper is put on the wearer, and are thus dimensioned to be able to absorb these loads.

It should be mentioned in this regard that the self-fastening type fasteners of the illustrated embodiment of the inventive pants-type diaper, and naturally also the weld or glue joins 12, 13, are subjected essentially to shear forces, which is the type of force against which self-fastening fasteners are highly resistant, and hence the joins 13 are not absolutely necessary from purely a strength aspect. However, it may nevertheless be convenient to provide a join 13 when manufacturing the pant diaper, so as to ensure that the fastening afforded by the self-fastening fastener is unbroken when the pant diaper is delivered and to prevent the self-fastening join from being subjected to unintentional peel forces when handling the pant diaper, the self-fastening fastener having low resistance to forces of this kind. An embodiment in which the self-fastening join is made safe or locked in the aforedescribed manner is preferred for these reasons.

As indicated in the aforegoing, the strength of the weld or glue joins 13 is not greater than the force at which the joins can be easily broken by the user without destroying the bands 11 or the outer casing sheet 3. This enables the pants-type diaper to be removed and changed, without needing to completely remove pants, trousers or like garments worn outside the diaper, by breaking the weld or glue joins 13 and releasing the self-fastener join between the bands 11 and the front side parts 7, 8, and therewith enable the rear part or the front part of the pant diaper to be inserted between the legs of the wearer. A pant diaper can be replaced, by breaking the weld or glue join 13 and releasing the self-fastening fastener between band and front side parts, whereafter the front or the rear part of the replacement pant diaper is inserted in between the legs of the wearer. The mutually opposing front and rear side parts are then fastened together, by refastening the released self-fastening fasteners, whereafter the pant diaper is drawn up to its final, correct position, in the same way as a pair of underpants, unless this has already been done when refastening the self-fastening fasteners.

FIGS. 2–5 are schematic views of parts of the front and rear side parts and fastening elements of pants-type diapers, these pant diapers differing from the pant diaper illustrated in FIG. 1 solely by virtue of the configuration of the fastener elements and the aforedescribed joins or fastenings. The same reference numerals as those used in FIG. 1 are also used to identify the side parts in FIGS. 2–5.

Figure 2:
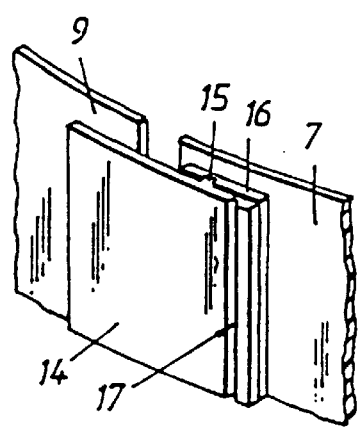
FIGS. 2–4 are schematic perspective views of parts of the side parts and fastener elements of a second, third and fourth embodiment of an inventive pants-type diaper.

The fastener element 14 of the FIG. 2 embodiment is comprised of a strip of flexible and elastic material, preferably a plastic material, which is either welded or glued to the side part 9. That part of the strip which overlaps its respective side part 7 presents an elongated and outwardly projecting bead or rib 15, which extends parallel with the side edge of the side part 7 and coacts with a groove having a form complementary to the rib 15 in a strip 16, this latter strip being securely affixed to the side part 7 in some suitable manner. The bead and the groove together form a releasable and refastenable fastening or join between the strip 14 and the side part 7. The strip 14 also includes a tear weakening in the form of a groove 17 which extends parallel with the edge 7 of the side part at some distance from the side edge of the part of strip 14 that overlaps the side part 7. That part of the strip 14 which lies between said side edge and the tear weakening 17 is fixedly attached to the underlying strip 16 in some suitable manner. Prior to tearing the bead-containing part 15 of the strip 14 loose from the strip 16, the releasable fastening or join is thus locked in principly the same manner as in the first described embodiment. According to one variant, the strips 14 and 16 may be moulded as a one-piece structure, wherein the tear weakening will function as a hinge when folding the strips 14, 16 together so as to obtain the configuration shown in FIG. 2.

Figure 3:
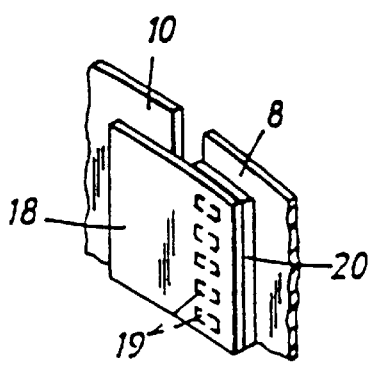

FIG. 3 illustrates a further embodiment which differs from the embodiment illustrated in FIG. 2 in that the fastener element, which is also in this case comprised of a plastic strip 18, is attached to the inside of the pant diaper instead of to the outside thereof, as is the case in the earlier described embodiments. That part of the strip 18 which overlaps its side part 8 includes a row of projections 19 which coact with recesses of complementary shape formed in a strip 20 which is firmly connected to the side part 8. The tips of some or all of the projections 19 are joined to the bottoms of respective recesses by means of a suitable weak join, such as an easily separated weld or glue join.

Figure 4:
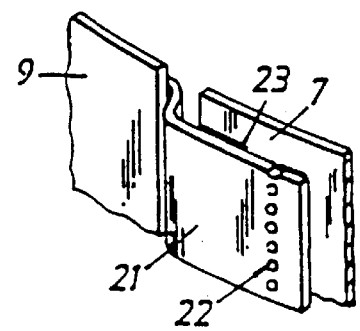

In the case of the embodiment illustrated in FIG. 4, the fastener element, in the form of a strip 21, is firmly joined to the inner surface of the side part 9 and releasably joined to the outer surface of the side part 7. The strip 21 also includes a tear weakening in the form of a row of perforations 22 which delimit an outer edge part of the strip, said edge part being welded or glued to the casing material of the side part 7. The strip 21 is also joined to the side part 7 by means of a releasable or refastenable join 23, which in this particular case is formed by an adhesive coating.

Figure 5:
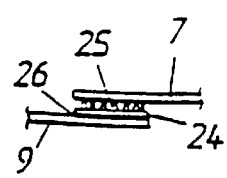
FIG. 5 is a schematic view simmilar to that from above of side parts and fastener elements of a fifth embodiment of an inventive pants-type diaper.

In the case of the embodiment illustrated in FIG. 5, the side parts 7 and 9 overlap one another and the fastener element lying between said parts is comprised of a self-fastening strip 24, one side of which presents outwardly projecting sponge-like elements 25 which engage the side part 7, the outer casing sheet of which side part is made of nonwoven material and therewith forms the female part of the self-fastening fastener, and the opposite side of which strip 24 is firmly glued or welded to the side part 9, as shown at 26. The self-fastener join may also in this case be strengthened with an easily released weld or glue join in the way described with reference to FIG. 1.

Although the aforedescribed and illustrated exemplifying embodiments have been directed solely to pants-type diapers, it will be understood that the invention can also be applied to sanitary panties, i.e. panties in which absorbent bodies are included for absorbing menstrual fluids and light incontinence discharges.

It will also be understood that the illustrated and described exemplifying embodiments can also be modified in many ways within the scope of the invention. For instance, other types of refastenable fasteners than those illustrated can be used, for instance button and buttonhole fasteners. The invention is therefore solely restricted by the scope of the following claims.

What is claimed is:

1. An absorbent article in the form of a diaper or sanitary panty, comprising:
    an elongated absorbent body enclosed between two casing sheets which casing sheets include two pairs of opposing front and rear side parts which at front and rear end parts of the absorbent body extend laterally beyond the absorbent body on both sides thereof,
    each of the pairs of the opposing front and rear side parts is joined together by means of a fastener element which is attached to one of said opposing side parts by a first join and releasably and refastenably fastened to the other of said opposing side parts by means of a second join which is weaker than the first join,
    the second join includes a first fastening which is destroyed when opening the second join for a first time, and also includes a second refastenable fastening which cannot be opened for a first time without destroying the first fastening.

2. An article according to claim 1, wherein the second join is stronger in a fastened state prior to being open the first time than when in a refastened state after being opened for the first time.

3. An article according to claim 1, wherein the first fastening of the second join is comprised of a weld; and the second fastening of said second join is comprised of a mechanical join.

4. An article according to claim 3 wherein the mechanical join is a self-fastening join.

5. An article according to claim 4, wherein the self-fastening join is comprised of a band of a male part of a self-fastening fastener, which male part includes a large number of hooks projecting from a surface thereof.

6. An article according to claim 1, wherein the first fastening of the second join is comprised of a glue join; and in that the second fastening is comprised of a mechanical join.

7. An article according to claim 1, wherein each fastener element is a discrete element from the front and rear side parts.

8. An article according to claim 7, wherein the first join is one of a weld or a glue join.

9. An article according to claim 7, wherein the first join and the first fastening are each one of a weld or a glue joint and the second fastening is a different kind of fastener than the first join and the first fastening.

10. An article according to claim 9, wherein the second fastening is a hook and loop fastener.

11. An article according to claim 9, wherein the second fastening is located between the first join and the first fastening.

12. An article according to claim 7, wherein the second fastening is located between the first join and the first fastening.

* * * * *